United States Patent [19]

Kanner et al.

[11] Patent Number: 5,277,198
[45] Date of Patent: Jan. 11, 1994

[54] BLOOD SAMPLING SYRINGE

[75] Inventors: Rowland W. Kanner, Guntersville; Francis E. Ryder, Arab, both of Ala.

[73] Assignee: Ryder International Corporation, Arab, Ala.

[21] Appl. No.: 920,036

[22] Filed: Jul. 27, 1992

[51] Int. Cl.$^5$ .............................. A61B 5/00
[52] U.S. Cl. .................................. 128/765
[58] Field of Search ............... 128/763, 765, 766, 770

[56] References Cited

U.S. PATENT DOCUMENTS

| | | | |
|---|---|---|---|
| 3,835,835 | 9/1974 | Thompson et al. | 128/765 |
| 3,890,956 | 6/1975 | Moorehead | 128/765 |
| 3,960,139 | 6/1976 | Bailey | 128/765 |
| 4,373,535 | 2/1983 | Martell | 128/765 |
| 4,813,433 | 3/1989 | Downey | 128/765 |

Primary Examiner—Max Hindenburg
Attorney, Agent, or Firm—Trexler, Bushnell, Giangiorgi & Blackstone, Ltd.

[57] ABSTRACT

A syringe for sampling bodily fluids, such as blood and the like, from a patient, comprises a first sleeve member and a second sleeve member disposed for relative shifting. The first sleeve member includes a first receiving chamber, and the second sleeve member includes a second receiving chamber. A needle mount is disposed on the first sleeve member for holding a needle in operative connection with the first receiving chamber so that bodily fluids can pass from the needle into the first receiving chamber. A filter is disposed in at least one of the first and the second sleeve members for permitting gas flow but prohibiting bodily fluid flow therethrough. The first receiving chamber communicates with the second receiving chamber through the filter so that relative shifting of the sleeve members causes gas within the first receiving chamber to flow through the filter into the second receiving chamber, thereby causing bodily fluid to flow into a first receiving chamber.

18 Claims, 2 Drawing Sheets

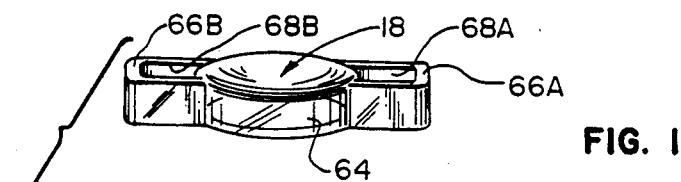
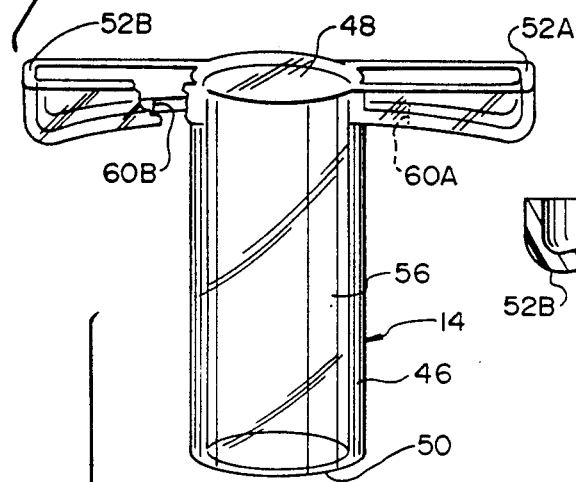
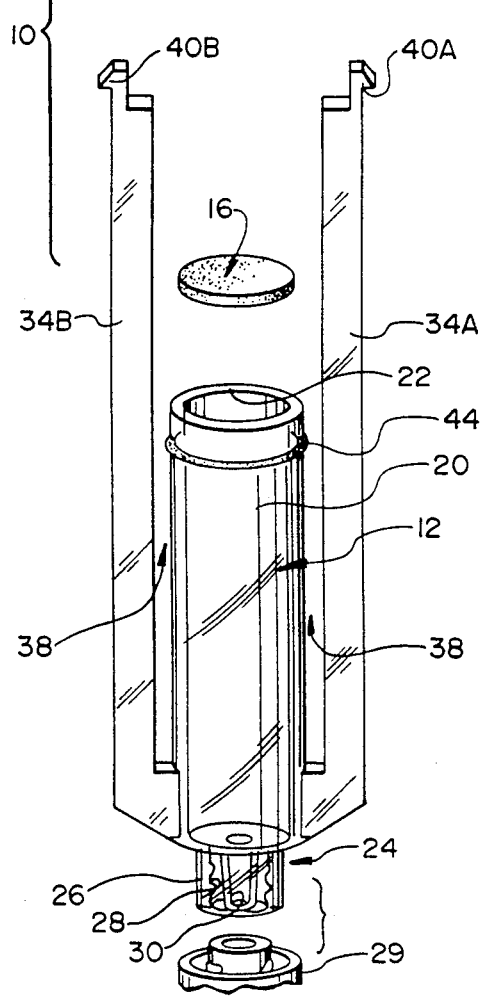
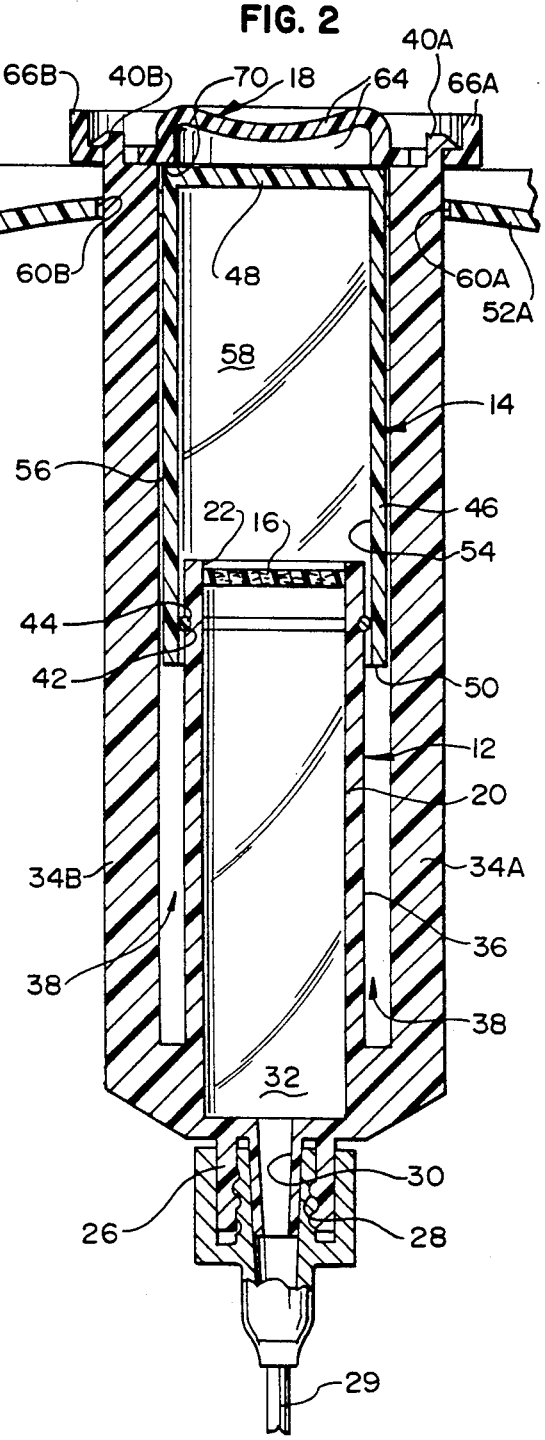
FIG. 1
FIG. 2

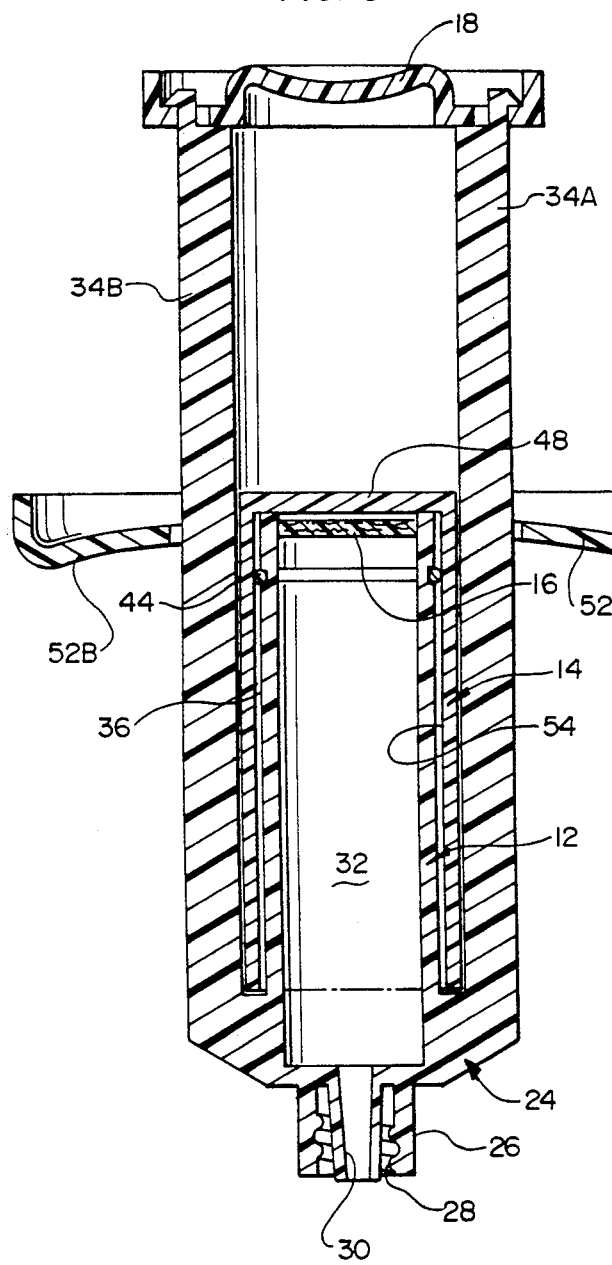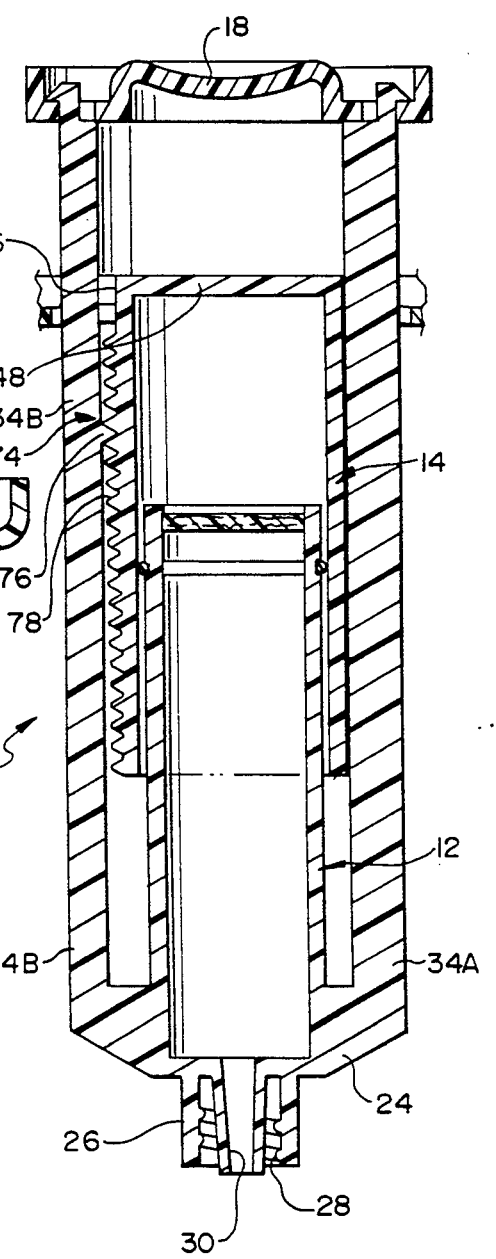

BLOOD SAMPLING SYRINGE

BACKGROUND AND SUMMARY OF THE INVENTION

The present invention generally relates to a novel sampling device for sampling blood, or the like. The invention more specifically relates to a novel blood sampling syringe for sampling or drawing blood from a patient which provides significant improvements over the blood sampling syringes of the prior art.

Many techniques and devices have been developed over the years for sampling blood and other bodily fluids from a patient. One such method is utilization of a standard hypodermic syringe. With this method, a hypodermic needle is attached to the syringe, with a piston of the syringe being in a collapsed position. The needle is then inserted through the skin and into a patient's blood vessel. To draw blood from the patient's vascular system, a technician must shift the piston into an extended position, thereby generating a negative pressure within the syringe which, when applied to the vascular system through the needle, draws blood into the syringe. The technician must be careful to shift the piston without removing the needle from the blood vessel while drawing blood in order to avoid injuring the patient.

While effective, this method presents some drawbacks which make it cumbersome to use. For example, to shift the syringe piston into the extended position, the technician often must grasp the syringe with two hands: one hand holding the main body of the syringe while the other shifts the piston.

In an effort to reduce these complications, other devices have been developed. One such device employs a substantially hollow housing upon which a hypodermic needle can be mounted, and a sealed pre-evacuated blood-receiving tube insertable into the housing for operative connection to the needle. In use, the needle is attached to the housing and is inserted into the patient's blood vessel. A portion of the needle extends through the housing and terminates in the hollow interior thereof. A pre-evacuated tube is inserted into the hollow interior such that the terminal end of the needle pierces the seal of the tube. Negative pressure present within the tube is applied through the needle to the patient's blood vessel, thereby drawing blood therefrom into the tube. When the tube is sufficiently full, the tube is removed from the hollow interior, thereby breaking the connection between the needle and the tube, and removing the negative pressure from the blood vessel.

While this device is effective, it also presents drawbacks in some instances which make it incompatible with some patients. Specifically, while the technician need not use both hands to draw blood into the tube, as opposed to the syringe method discussed hereinabove, use of both hands is required when inserting the pre-evacuated tube and removing the filled tube so that the needle will not be dislodged from the blood vessel.

Utilization of the pre-evacuated tube itself can present other problems. Because the tube has been pre-evacuated, the negative pressure applied to the patient is applied rapidly and is not regulated, and the technician lacks control of the rate of blood drawn from the patient's vascular system. For elderly or infant patients who may have delicate or fragile blood vessels, or those who suffer from a vascular disease, their blood vessels may collapse because of the application of unregulated negative pressure, resulting in serious harm to the patient. The pre-evacuated tube also prevents reversal of the blood draw, which may be necessary in some circumstances.

Another improvement in devices for sampling blood is disclosed in the patent to Downey, U.S. Pat. No. 4,813,433, viz. a different construction for a sampling syringe. This syringe generally comprises a hollow tube bifurcated diametrically along an axial length thereof by a partition wall to form two substantially half-cylindrical chambers. A semi-circular piston is shiftably disposed within one chamber which communicates with the other, to which a hypodermic needle is connected, through an aperture in the partition wall. In this manner, as the piston properly shifts within one chamber, a negative pressure is generated in the other chamber, thereby drawing blood into that chamber from the patient.

While this device is also effective, it too presents certain drawbacks. Because this device is also basically a syringe, it has the same two-handed operational requirements and limitations discussed in detail hereinabove. Furthermore, the bifurcated structure of the syringe is cumbersome and expensive to manufacture and difficult to mold from a plastic material. These manufacturing difficulties result in the syringe having an increased cost, thereby reducing the economic disposability thereof. In addition, it is relatively difficult to form and maintain a seal around the semicircular piston required with this design, which further increases the cost of the syringe, as well as making it more complicated to operate.

The novel blood sampling syringe of the present invention is intended to solve some, if not all, of the problems presented by the blood sampling methods and devices of the prior art discussed above. Specifically, the blood sampling syringe of the invention provides for one-handed, controlled negative pressure blood draw from a patient. This syringe allows a technician to gently apply negative pressure to a patient's vascular system. The technician can regulate negative pressure application while also being able to reverse the blood flow in the syringe, if necessary. This novel syringe comprises relatively few parts, is relatively easily and inexpensively molded and manufactured, and is therefore economically disposable.

OBJECTS AND SUMMARY OF THE INVENTION

A general object of the present invention is to provide a novel sampling device for blood or other fluids.

A more specific object of the invention is to provide a novel blood sampling syringe which allows for the controlled application of a blood-drawing negative pressure to a patient's vascular system which is gentler than the negative pressures applied by some of the blood sampling syringes of the prior art.

Another object of the present invention is to provide a novel blood sampling syringe that allows for one-handed operation thereof.

An additional object of the invention is to provide a novel blood sampling syringe which allows for controlled blood draw from a patient.

A further object of the present invention is to provide a novel blood sampling syringe which positively stops application of negative pressure to a patient's vascular system for preventing overdraw of blood therefrom.

Yet another object of the invention is to provide a novel blood sampling syringe which provides a technician with enhanced tactile feel and an auditory indication of negative pressure applied by the syringe.

A novel sampling syringe, for sampling blood or other bodily fluids from a patient, constructed according to the teaching of the present invention, comprises a first sleeve or tube member and a second sleeve or tube member disposed for relative shifting. The first sleeve member includes a first receiving chamber, and the second sleeve member includes a second receiving chamber. A needle mount is disposed on the first sleeve member for holding a needle in operative connection with the first receiving chamber so that bodily fluids can pass from the needle into the first receiving chamber. A filter is disposed in at least one of the first and the second sleeve members for permitting gas flow but prohibiting bodily fluid flow therethrough. The first receiving chamber communicates with the second receiving chamber through the filter so that relative shifting of the sleeve members causes gas within the first receiving chamber to flow through the filter into the second receiving chamber, thereby causing bodily fluid to flow into the first receiving chamber.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which:

FIG. 1 is an exploded perspective view of a novel blood sampling syringe, constructed according to the teachings of the present invention;

FIG. 2 is a sectioned elevational view of the syringe of FIG. 1 with the syringe being in an extended position;

FIG. 3 is a view, similar to that of FIG. 2, with the syringe in a collapsed position; and FIG. 4 is a sectioned elevational view of an alternative embodiment of the invention having means for providing enhanced tactile feel and for producing an auditory indication of negative pressure applied by the syringe.

DETAILED DESCRIPTION OF A PREFERRED EMBODIMENT

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Referring initially to FIG. 1, a novel sampling device or blood sampling syringe 10, constructed according to the teachings of the present invention, is shown in exploded perspective form. While the syringe 10 will be discussed with relation to its employment in drawing blood from a patient, it is envisioned that the syringe 10 can be successfully employed in drawing or sampling other fluids without departing from the scope of the invention.

As illustrated in FIG. 1, the syringe 10 generally comprises four main elements: a main or first tube or sleeve member 12, and a secondary tube or sleeve member 14, a filter 16 and a cap member 18. The members 12, 14, and 18 are preferably molded from a suitable plastic material, such as polypropylene or the like. By molding the members 12, 14 and 18 from plastic, the syringe 10 is relatively inexpensive, thereby rendering it economically disposable. The filter 16 is preferably a substantially disk-shaped portion of hydrophobic filter media, such as that commonly known as Porex TM, the significance of which will become more apparent from the discussion to follow.

The structures of the members 12, 14, and 18 will be discussed with reference to FIGS. 1, 2 and 3. The member 12 generally comprises a substantially cylindrical tube 20 having an open upper end 22 and an enlarged base portion 24 on opposite axial ends thereof. Means for allowing blood flow into the member 12 in the form of a hypodermic needle mount 26, including threads 28 for threadibly accepting a hypodermic needle assembly 29, depends from the base portion 24. The base portion 24 further includes a tapered bore 30 having a diameter which gradually decreases from a juncture of the bore 30 with a receiving chamber or interior 32 of the tube 20, as the bore 30 extends through the mount 26. Thus, blood can pass through the needle 29 and the bore 30 into the interior 32 of the tube 20.

Bifurcated handle portions 34A and 34 extend from the base portion 24 away from the mount 26 spaced from tube 20 and substantially parallel to an axis of elongation of the tube 20 along diametrically opposite sides thereof. The handle portions 34A and 34B have a length substantially longer than the axial length of the tube 20, and the portions 34A and 34B are radially offset from the outer cylindrical wall 36 of the tube 20 to define spaces 38, the significance of which will be discussed in detail hereinafter.

The ends of the handle portions 34A and 34B opposite to the ends thereof defined by the base portion 24 terminate in projecting tabs 40A and 40B, respectively, for forming a snap-fit between the member 12 and the cap member 18 to mount the cap member 18 to the upper ends of said handle portion, see FIG. 2. The plastic forming the member 12 has sufficient elasticity to allow the tabs 40A and 40B to flex into engagement with mating structures on the cap 18, as will be discussed later.

The tube 20 also includes an annular recess or groove 42 proximate to the open end 22 for accepting sealing means in the form of an O-ring 44, preferably constructed from a suitable elastomeric material, such as rubber and the like. The O-ring 44 forms a seal between the outer sleeve member 12 and the inner sleeve member 14, and permits a vacuum to be drawn upon relative movement between the sleeve or like members 12 and 14. The interior 32 of the tube 20 is defined by a diameter somewhat smaller than a diameter of the filter 16. This allows the filter 16 to be press-fitted into the interior 32 at a location preferably between the recess 42 and the open end 22. The filter 16 extends across the entirety of the interior 32 at that location. Due to the hydrophobic nature of the filter 16, the filter 16 allows air to pass freely therethrough into and out of the interior 32, while preventing flow of blood or other bodily fluid therethrough and beyond the open end 22. Thus, blood drawn from a patient can be positively retained within the interior 32 between the filter 16 and the mount 26.

The structure of the inner sleeve member 14 is also visible in FIGS. 1, 2 and 3. The sleeve member 14 generally comprises a substantially cylindrical tube 46 having a closed end 48 and an open end 50 on opposite axial ends thereof. Finger grip portions 52A and 52B extend radially outwardly from the tube 46 proximate the closed end 48 which cooperate with the cap member 18 for facilitating operation of the syringe 10, as will be discussed further hereinafter. The tube 46 also has an inner cylindrical wall surface 54 and an outer cylindrical wall surface 56. The inner wall surface 54 is defined by a diameter slightly larger than a diameter defining the wall 36 of the tube 20, while the outer wall surface 56 is defined by a diameter slightly smaller than a diameter which defines the offset relationship of the handle portions 34A and 34B.

Accordingly, the thickness of the tube 46 is somewhat smaller than the width of the spaces 38 between handle portion 34A and 34B and the tube wall 20, thereby allowing the inner sleeve member 14 to be slidably disposed within the spaces 38 and about the tube 20 which is coaxially located within a receiving chamber or interior 58 of the tube 46, as illustrated in FIGS. 2 and 3. The interior 32 of the first tube 12 communicates with the interior 58 of the second tube 14 across the filter 16.

To facilitate the above disposition, the finger portions 52A and 52B respectively include apertures 60A and 60B for slidably accepting the handle portions 34A and 34B. Thus, when the members 12 and 14 are properly assembled, the wall 36 opposes the inner surface 54 while the outer surface 56 opposes the handle portions 34A and 34B. The inner surface 54 is also in sliding engagement with the O-ring 44. Accordingly, the O-ring 44 forms an air-tight seal between the interior 32 and the interior 58. The open end 22 of the tube 20 and an annular portion 62 act as positive stops for positively limiting relative axial shifting of the members 12 and 14 between a first or collapsed position, shown in FIG. 3, and a second or extended position of FIG. 2, as will be discussed in greater detail later.

The cap member 18 generally comprises a substantially circular disk portion 64 and a pair of radial projections 66A and 66B extending from the portion 64. The portion 64 and the projections 66A and 66B are intended to be contacted by a technician's palm or thumb for facilitating relative axial shifting of the members 12 and 14. Apertures 68A and 68B are disposed through the projections 66A and 66B and are configured and located for lockingly accepting the tabs 40A and 40B, respectively. The cap member 18 further includes a positive stop portion 70 for limiting relative axial shifting of the members 12 and 14. To complete assembly of the syringe 10, after the member 14 is disposed within the space 38 as discussed hereinabove and as illustrated in FIGS. 2 and 3, the cap member 18 is snap-fitted onto the member 12 by pressing the tabs 40A and 40B through the apertures 68A and 68B. Once through the apertures 68A and 68B, the tabs 40A and 40B lock against a side of the projections 66A and 66B, respectively, opposite to the stop portion 70.

A modified embodiment of the invention, syringe 72, is illustrated in FIG. 4. The syringe 72 is substantially similar to the syringe 10, as is indicated by the like reference numerals, except for the differences to be noted hereinbelow. Specifically, the syringe 72 has rachet means 74 for providing a technician with enhanced tactile feel as well as an auditory indication of the reduced or negative pressure applied by the syringe 72 to the patient's vascular system. It is to be noted that the rachet means 74 is constructed to function equally well both during shifting the syringe 10 from the collapsed to the extended position and the reverse.

In the illustrated embodiment, the rachet means 74 comprises a tooth-like projection 76 which extends laterally from the handle portion 34B, respectively, inwardly towards the wall 36 of the tube 20 at a predetermined location on the portion 34B. The projection 76 cooperates with a substantially linear series of complimentary tooth-like projections 78 on the inner sleeve or tube member 14 which project outwardly away from the outer wall surface 56 and extend along a predetermined, effective axial length of that surface 56.

The location of the projection 76 and the length of the series of projections 78 along the axis of elongation of the member 14 are predetermined such that the projection 76 constantly engages the projection 78 as the members 12 and 14 are relatively axially shifted between the extended and the collapsed positions. The plastic material provides the projections 76 and 78 with sufficient flexibility for allowing the projections 76 and 78 to flex into and out of interengagement responsive to relative axial shifting of the members 12 and 14. As the projections 76 and 78 flex into and out of interengagement, an auditory signal is produced, indicative of the negative pressure applied to the patient. Also, the rachet means 74 provides the technician with an increased tactile feel responsive to the negative pressure.

With the construction of the syringe 10 being disclosed in detail hereinabove, the operation thereof will now be discussed. Again, while the operation of the syringe 10 will be discussed with its employment in drawing blood from a patient, it is to be clearly understood that the syringe 10 can be effectively utilized in a number of different employments by different operators without departing from the scope of the invention. Also, because the methods of preparation of a patient for a blood draw, mounting of a needle on the needle mount 26, and properly inserting the needle into a patient's vascular system are well known in the relevant art, those methods will not be discussed herein. Accordingly, the operation of the syringe 10 will be discussed with an understanding that those methods have already been performed. Also, it is to be noted that the syringes 10 and 72 function substantially similarly.

The syringe 10 is in the collapsed or initial position, illustrated in FIG. 3 and is connected to a needle assembly 29 (not shown in FIG. 3). The needle assembly 29 in turn is inserted into a patient's vascular system. The technician grasps the syringe 10 with one hand by placing either his thumb or palm in contact with the disk portion 64 of the cap member 18, and by simultaneously placing his fingers, preferably the pointer and the index fingers, in appropriate contact with the projections 52A and 52B on the member 14. By assuming this appropriate positioning, the technician is able to operate the syringe 10 with only one hand to produce relative movement between sections 12 and 14 to apply negative pressure to the needle assembly 29.

As shown in FIG. 3, the collapsed or initial position is defined by the confrontation of the open end 22 of the member 12 with the closed end 48 of the member 14. Also, the open end 50 of the member 14 may confront the annular portion 62 of the base portion 24 of the member 12. In this way, the ends 22 and 48, and the end 50 and the portion 62 can act as positive stop members for positively limiting relative axial shifting of the members 12 and 14. In this position, the interior 32 of the tube 20 is filled with air, thereby preventing appreciable blood flow from the patient's vascular system into the syringe 10. If the syringe 72 having rachet means 74 is used, the disposition of the means 74 is predetermined so that the projections 76 and 78 are in interengagement. As the technician relatively axially shifts the members 12 and 14, the projections 76 and 78 will successively engage to provide audio and tactile feedback.

To draw blood from the patient, the technician flexes his fingers towards his palm or thumb. These finger movements cause the members 12 and 14 to relatively axially shift towards the extended or final position of FIG. 2. As this shifting occurs, the closed end 48 of the member 14 moves farther and farther away from the open end 22 of the member 12. The air within the interior 32 of the tube 20 is drawn through the filter 16 and into the interior 58 of the tube 46. The seal provided by the O-ring 44 insures that the air drawn into the interior 58 comes only from the interior 32 through the filter 16, and not form an ambient atmosphere. Thus, the volume of air drawn from the interior 32 into the interior 58 is replaced by a corresponding volume of blood drawn from the patient.

As the members 12 and 14 are progressively shifted, a negative pressure is generated within the interior 32, which is applied to the patient's vascular system through the needle assembly 29. The application of this negative pressure causes blood to be drawn from the patient into the interior 32. Because the negative pressure is generated by the technician's hand movements, the syringe 10 is able to apply a controlled, variable negative pressure to the patient's vascular system. Thus, the application of negative pressure can be as gentle as necessary. This is particularly important for patients who have weak blood vessels or vascular disease. Collapse of the patient's blood vessels during the blood draw can be eliminated by proper manipulation of the syringe 10 by the technician because the technician can directly regulate blood flow rate into the syringe 10. If the syringe 72 having rachet means 74 is used, then the technician is provided with a greater tactile feel responsive to the degree of negative pressure applied to the patient and an auditory indication of that degree of negative pressure, thereby allowing the technician to more carefully monitor the rate of blood flow into the interior 32. Also, the syringe 10 is reversible, allowing the technician to account for unexpected problems that may arise during a blood draw.

The technician draws more and more blood as the members 12 and 14 are axially shifted, separating the open end 22 of the tube 20 from the closed end 48 of the tube 46 by a progressively greater distance. The filter 16 allows air within the interior 32 of the tube 20 to flow into the interior 58 of the tube 46. However, the hydrophobic nature of the filter 16 prevents blood or other fluid located within the interior 32 from flowing therethrough and into the interior 58. Furthermore, to prevent blood flow into the interior 58 and to prevent overdraw of blood from the patient, the extended position is defined by confrontation of the closed end 48 of the member 14 with the positive stop portion 70 on the cap member 18. The stop portion 70 prevents the members 12 and 14 from being axially shifted beyond the extended position, thereby limiting the amount of blood that can be drawn into the interior 32.

At any time, the technician can reverse the direction of blood flow into the interior 32 by appropriate force application to the finger portions 52A and 52B and the cap member 18, thereby reversing direction of axial shifting of the members 12 and 14. If blood flow reversal is desired, then the reversed axial shifting of the members 12 and 14 causes the volume of air disposed within the interior 58 to be forced back through the filter 16 and into the interior 32, thereby displacing blood in the interior 32. Resumption of blood draw can also occur at any time by inducing appropriate relative axial shifting of the members 12 and 14. The rachet means 74 does not affect the ability of the members 12 and 14 to shift in either direction, and further provides increased tactile feel and auditory indications irrespective of shift direction, thereby allowing the technician to more precisely monitor and control the blood draw from the patient.

The syringes 10 and 72 of the present invention hereintofore disclosed are significant improvements over the blood sampling devices of the prior art. The syringes 10 and 72 allow for application of a controlled fluid-drawing negative pressure to a vascular system which is gentler than the negative pressures applied by some of the prior art devices. The syringes 10 and 72 are one-handed operable, and can have means for providing an operator with enhanced tactile feel and an auditory indication of negative pressure applied by the syringe 72. Furthermore, because the syringes 10 and 72 comprise only five parts, viz. the members 12, 14, and 18, the filter 16 and the O-ring 44, and because these parts are composed of relatively inexpensive materials, the syringes 10 and 72 are relatively inexpensive, as compared to some of the devices of the prior art, and is economically disposable.

While preferred embodiments of the present invention are shown and described, it is envisioned that those skilled in the art may devise various modifications of the present invention without departing from the spirit and scope of the appended claims.

The invention claimed is:

1. A syringe for sampling bodily fluids, such as blood or the like, from a patient, said syringe comprising: a first sleeve member and a second sleeve member disposed for relative shifting; said first sleeve member including a first receiving chamber, and said second sleeve member including a second receiving chamber said first receiving chamber being relatively shiftably disposed within said second receiving chamber; sealing means being disposed between said first receiving chamber and said second receiving chamber for sealing engagement therebetween; means for mounting a needle associated with said first sleeve member for holding a needle in operative connection with said first receiving chamber so that bodily fluids can pass from a needle into said first receiving chamber; filter means disposed in at least one of said first and said second sleeve members for permitting gas flow but prohibiting bodily fluid flow therethrough; said first receiving chamber communicating with said second receiving chamber through said filter means; and proper relative shifting of said sleeve members causing gas within said first receiving chamber to flow through said filter means into said second receiving chamber, thereby causing bodily fluid to flow into said first receiving chamber.

2. A syringe as defined in claim 1, wherein the filter means comprises a piece of hydrophobic filter media.

3. A syringe as defined in claim 1, further comprising means operatively connected to the first sleeve member and the second sleeve member for facilitating one-handed relative shifting of said first sleeve member and said second sleeve member.

4. A syringe as defined in claim 3 wherein the means comprises a portion operatively connected to at least one of said first sleeve member and said second sleeve member for engagement with an operator's fingers and another portion connected to another of said first sleeve member and said second sleeve member for engagement with at least one of an operator's palm and thumb.

5. A syringe as defined in claim 1, further comprising means operatively associated with the first sleeve member and the second sleeve member for providing an operator with increased tactile feel and an auditory indication of bodily fluid flow in said first receiving chamber.

6. A syringe as defined in claim 5, wherein said means comprises interengaging projections extending from said first sleeve member and said second sleeve member.

7. A syringe as defined in claim 1, further comprising positive stop means on at least one of said first sleeve member and said second sleeve member for positively limiting relative shifting between the first position and the second position.

8. A syringe for sampling blood from a patient, the syringe comprising: an inner tube and an outer tube coaxially disposed for relative axial shifting; means operatively connected to the inner tube for allowing blood flow into said inner tube responsive to the axial shifting; hydrophobic filter means operatively connecting said inner tube to said outer tube for permitting gas flow and for prohibiting blood flow to and from said inner tube into and out of said outer tube responsive to said axial shifting; a reduced pressure generated in the inner tube by gas flow from said inner tube into said outer tube through said filter means; the reduced pressure causing blood to flow from said means for allowing blood flow into said inner tube; and manipulation means operatively connected to said inner tube and said outer tube for facilitating said axial shifting.

9. A syringe as defined in claim 8, wherein the inner tube has an open end, opposite to the means for allowing blood flow, which opens into the outer tube; the filter means comprising a piece of hydrophobic filter media filling said inner tube adjacent the open end; the outer tube comprising a closed end variably offset from the open end responsive to the axial shifting; and sealing means disposed between said inner tube and said outer tube for sealing engagement therebetween.

10. A syringe as defined in claim 9, further comprising positive stop means formed by engagement of the open end with the closed end for positively limiting the axial shifting.

11. A syringe as defined in claim 8, wherein the manipulation means comprises a base connected to said inner tube for engagement with at least one of an operator's thumb and palm, and a projection extending from said outer tube for engagement with an operator's finger.

12. A syringe as defined in claim 8, further comprising positive stop means for positively limiting the axial shifting.

13. A syringe as defined in claim 8, wherein the manipulation means comprises a bifurcated handle extending axially along said inner tube, and a projection substantially radially extending from the outer tube; a space defined by the handle and the inner tube of dimensions sufficient for accepting the outer tube; the outer tube being shiftably disposed within said space; and positive stop means further defining said space for positively limiting said axial shifting.

14. A syringe as defined in claim 8, further comprising means operatively associated with the inner tube and the outer tube for providing an operator with increased tactile feel and an auditory indication of blood flow in said inner tube.

15. A syringe as defined in claim 14, wherein said means for providing increased tactile feel comprises interengaging projections extending from said inner tube and said outer tube.

16. A device for sampling fluids comprising: a first tube and a second tube coaxially disposed for relative axial shifting; means operatively connected to the first tube for allowing fluid flow into said first tube; filter means operatively connecting said first tube with said second tube for allowing gas flow and for prohibiting fluid flow from said first tube into said second tube responsive to relative axial shifting of said first tube and said second tube; said relative axial shifting generating a reduced pressure within said first tube by drawing gas through the filter means from said first tube into said second tube; and the reduced pressure drawing fluid into said first tube.

17. A device as defined in claim 16, further comprising manipulation means connected to the first tube and the second tube for allowing relative axial shifting.

18. A device as defined in claim 16, further comprising means connected to the first tube and the second tube for providing increased tactile feel and an auditory indication of the reduced pressure drawing fluid into said first tube.

* * * * *